United States Patent [19]

O'Donnell

[11] Patent Number: 5,041,134
[45] Date of Patent: Aug. 20, 1991

[54] INTRAOCULAR LENS ASSEMBLY

[76] Inventor: Francis E. O'Donnell, 6035 Lindell Blvd., St. Louis, Mo. 63112

[21] Appl. No.: 392,595

[22] Filed: Aug. 11, 1989

[51] Int. Cl.[5] .............................................. A61F 2/16
[52] U.S. Cl. ...................................................... 623/6
[58] Field of Search ............................................ 623/6

[56] References Cited

U.S. PATENT DOCUMENTS

| | | | |
|---|---|---|---|
| 4,056,855 | 11/1977 | Kelman | 623/6 |
| 4,608,049 | 8/1986 | Kelman | 623/6 |
| 4,693,716 | 9/1987 | Mackool | 623/6 |
| 4,813,954 | 3/1989 | Siepser | 623/6 |
| 4,834,753 | 5/1989 | Sulc et al. | 623/6 |

FOREIGN PATENT DOCUMENTS

| | | | |
|---|---|---|---|
| 0194390 | 9/1986 | European Pat. Off. | 623/6 |
| 3503690 | 11/1986 | Fed. Rep. of Germany | 623/6 |
| 3626869 | 2/1988 | Fed. Rep. of Germany | 623/6 |

Primary Examiner—Ronald Frinks
Attorney, Agent, or Firm—Paul M. Denk

[57] ABSTRACT

An intraocular (IOL) assembly for implanting in the posterior chamber of a human eye after an extracapsular extraction is disclosed. The IOL assembly includes an optic holder having haptic elements for locating and positioning the optic holder in fixed position within the posterior chamber of the eye and an optic lens releasably secured to the optic holder for interchange of different optic lens as needed, without removing the entire optic holder from the eye. Haptic elements include flexible and resilient haptic elements with reversely curving free ends for implanting the optic holder within the posterior chamber. For releasably securing the optic lens to the optic holder, several different mechanical and/or adhesive constructions or techniques may be employed. When it is desired to change an optic lens, it is a simple matter to releasably remove the optic lens from the optic holder and replace the removed optic lens with the new optic lens desired by also releasably securing the same in position relative to the optic holder.

1 Claim, 1 Drawing Sheet

INTRAOCULAR LENS ASSEMBLY

BACKGROUND OF THE INVENTION

The present invention relates to an intraocular lens (IOL) assembly, and more particularly, to an IOL assembly for implanting in the posterior chamber of a human eye after an extra capsular extraction.

In cataract surgery following extracapsular extraction of a cataractous lens, an intraocular lens (IOL) may be implanted. Various types of such lens, together with different implantation sites within the eye, have been proposed. It has been suggested that a lens may be implanted in the anterior chamber, the posterior chamber or in the pupilar space of an eye. Although the anterior chamber is most readily accessible for lens implantation, unless the lens is carefully sized or precisely fitted, it may not be supported at the desired angle or may otherwise traumatize the cornea. Mounting a lens within the pupilar space is also undesirable, but for different reasons. It has been discovered that while lens centering may not be a problem, the support of the lens within the pupilar space itself may be poor and/or the iris may not be dialated when desired. Because of the above disadvantages and further because the original lens is located in the posterior chamber of the eye, the posterior chamber is considered the most advantageous for IOL implantation.

While the posterior chamber is most desirable for IOL implantation, it is the most difficult and least accessible area for implementation and lens fixation. Through the development of various flexible and resilient haptic elements associated with an IOL, the problems associated with the initial implementation of an IOL in the posterior chamber of an eye have been overcome.

Even though initial IOL implementation may be successful, there are circumstances in which it would be desirable to replace the IOL initially implanted in the eye due to changes and/or deterioration in the eyes of an implant wearer, improvements in optic function (such as bifocality), and correction of unwanted refractive error. At the present, this requires removing the entire IOL implant and replacing it with a new desired implant. As will be appreciated, removing the old IOL implant and replacing it with a new one creates unneccessary trauma during surgery, in addition to the fact that it is difficult to perform.

SUMMARY OF THE INVENTION

Among the several objects and advantages of the present invention include:

The provision of a new and improved IOL assembly which overcomes the aforenoted deficiencies and problems associated with prior art devices;

The provision of the aforementioned IOL assembly which includes an optic lens that is releasably secured to an optic holder to facilitate interchange of different optic lens as needed, without removing the entire optic holder;

The provision of the aforementioned IOL assembly which is a two-part component; namely, an optic holder and a separate optic lens which is releasably secured to the optic holder for removal and replacement as needed;

The provision of the aforementioned IOL assembly including an optic holder which is fixedly secured in place within the posterior chamber of an eye by the use of flexible and resilient haptic elements;

The provision of the aforementioned IOL assembly where the optic lens may be releasably secured to the optic holder through a variety of mechanical and/or adhesive techniques or constructions; and The provision of the aforementioned IOL assembly which is simple and easy to make and install; facilitates quick and easy replacement of optic lens; minimizes injury to the eye occasioned by unnecessary surgical procedures; allows the implant wearer to use an updated or more effective optic lens as needed; reduces the time and cost of surgical implantations; and is otherwise well adapted for the purpose intended.

Briefly stated, the intraocular lens (IOL) assembly of the present invention includes the implanting of the IOL assembly in the posterior chamber of a human eye after extracapsular extraction. The IOL assembly includes and optic holder having haptic means for locating and positioning the optic holder in fixed position within the posterior chamber of the eye, and an optic lens releasably secured to the optic holder for interchange of different optic lens as needed, without removing the entire optic holder.

In the IOL assembly, the haptic means associated with the optic holder includes flexible and resilient haptic elements which are integrally attached to the optic holder for implanting the optic holder within the posterior chamber. Preferably, there are two generally opposed flexible and resilient haptic elements with reversely curving free ends associated therewith.

The optic lens may be mechanically releasably secured to the optic holder. Some examples include an optic lens and optic holder having complementary interfitting fastener means for securing the optic lens and optic holder together. Complementary interfitting fastener means may include complementary interfitting male and female elements. Another mechanical approach includes a circumferential depression formed in the optic holder for receipt of an outer free end of the optic lens. Still another mechanical construction includes manufacturing the optic lens from a material which will cause the optic lens to swell into engagement with the optic holder when brought into engagement therewith. A still further mechanical means includes threaded fastening means interconnecting the optic lens and optic holder to each other.

The optic lens may be releasably secured to the optic holder through releasable adhesive constructions, which may also include a biological glue readily adaptable to the implant user's eye.

The optic holder may be made from foldable or nonfoldable material such as from polymethylmethacylate, PROLENE(polypropylene), hydrogel or silicone material. The optic lens may be made from polymethymethacrylate, polycarbonate, hydrogel or silicone material.

These and other objects and features of the present invention will become apparent from the description that follows.

BRIEF DESCRIPTION OF THE DRAWINGS

In the drawings.

Corresponding reference numerals will be used throughout the various figures of the drawings.

DESCRIPTION OF THE PREFERRED EMBODIMENTS

The following detailed description illustrates the invention by way of example and not by way of limitation. This description will clearly enable one skilled in the art to make and use the invention, and describes several embodiments, adaptions, variations, alternatives and uses of the invention, including what I presently believe is the best mode of carrying out the invention.

Figure 1:
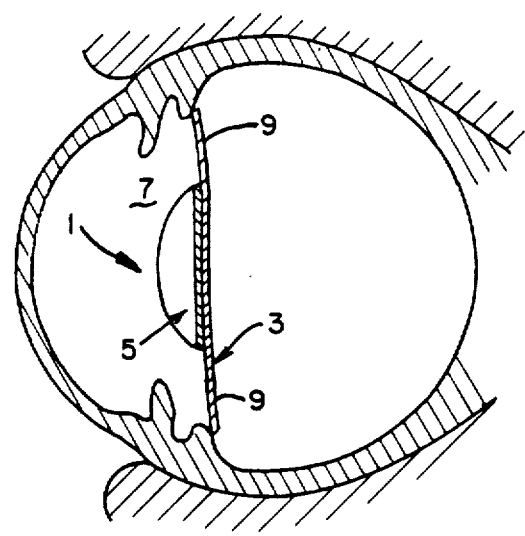
FIG. 1 is a cross sectional view of an eye showing an intraocular lens (IOL) assembly of the present invention located in the posterior chamber of the eye.
Figure 2:
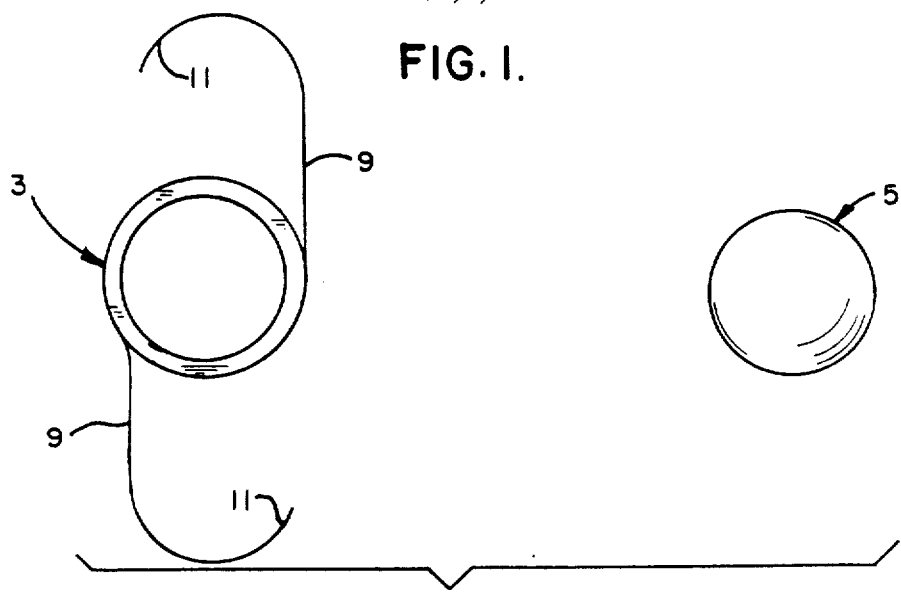
FIG. 2 is an exploded top plan view of an IOL assembly including an optic holder having integral haptic elements associated therewith and an optic lens constructed to be releasably secured to the optic holder according to any one of the various techniques shown in FIGS. 3-7.

In the drawings, FIG. 1 shows the environment in which the IOL assembly 1 of the present invention is implanted into the posterior chamber of an eye, FIG. 2 shows the optical holder 3 and optic lens 5 forming the IOL assembly 1, and FIGS. 3-7 show various constructions and techniques for releasably securing and mounting the optic lens 5 to the optic holder 3.

The IOL assembly 1 shown in FIG. 1 of the drawings, including the releasably secured optic holder 3 and optic lens 5, are shown as being mounted in the posterior chamber 7 of an eye, through the use of flexible and resilient haptic elements 9, 9 integrally attached to the optic holder 3. As is well known in the art, generally opposed flexible and resilient haptic elements 9, 9, as best seen in FIG. 2 of the drawings, with reversely curving free ends 11, 11 are utilized to implant the optic holder 3 within the posterior chamber 7 of an eye, with the flexible and resilient haptic elements 9, 9 and reversely curving free ends 11, 11 thereof serving to retain the optic holder in the desired position in the posterior chamber 7 of the eye, as is well known.

The combined optic holder 3 with haptic elements 9, 9 are manufactured, as shown in FIG. 2 of the drawings, as a one-piece unit, or may be manufactured as a multipiece unit and subsequently assembled together as a single optic holder 3 unit. The optic holder, with or without the integral haptic elements 9, 9, may be made from foldable or nonfoldable material including polymethylmethacylate, PROLENE(polypropylene), hydrogel or silicone.

The optic holder is constructed to be inserted and implanted within the posterior chambers 7 of an eye only once, whereas the optic lens 5, according to the teachings of the present invention, may be changed due to various conditions within an eye. Initially, after the direct intraocular lens power is confirmed intraoperatively, the optic lens 5 is releasably secured to the optic holder 3, by any of the construction or techniques illustrated in FIGS. 3-7 of the drawings.

The optic lens may also be made from any foldable material such as hydrogel or silicone, or nonfoldable material such as polymethylmethacrylate or polycarbonate, as desired.

As shown in FIGS. 3-7 of the drawings, there are numerous ways of releasably securing or mounting the optic lens 5 relative to the optic holder 3 in order to permit removal of a particular optic lens 5 for replacement with the correct intraocular power, due to changing conditions of an eye. For this purpose, the various constructions and techniques illustrated in FIGS. 3-7 may be employed.

The different embodiments of the invention shown in FIGS. 3-7 of the drawings are distinguished from one another by employing a different letter suffix in consecutive sequence, together with the numbered sequence 3 and 5 to identify the optic holder and optic lens, in each case, respectively.

Figures 3, 4, 5, 6, 7:
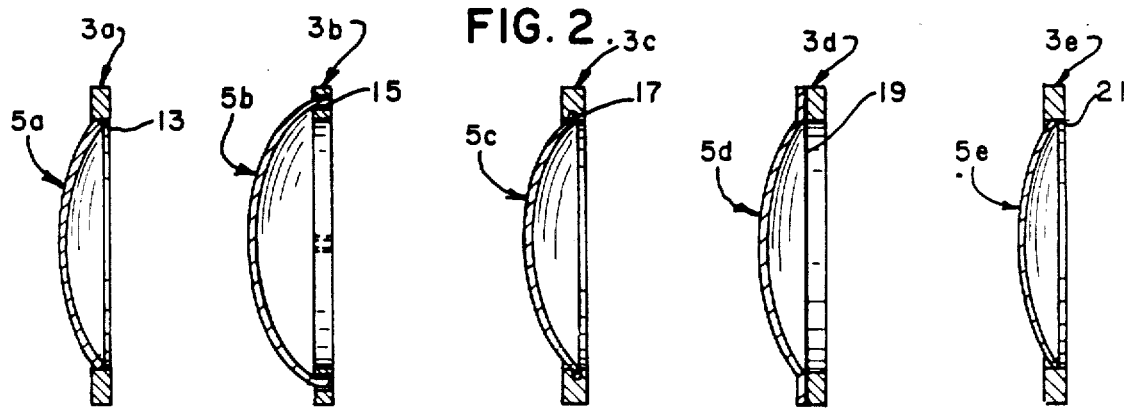
FIG. 3 is a sectional view of the IOL assembly and illustrating one construction or technique for mechanically securing the optic lens relative to the optic holder.
FIG. 4 illustrates another construction or technique for securing the optic lens to the optic holder including complementary interfitting fasteners.
FIG. 5 is a sectional view of still another IOL assembly showing a different construction or technique for securing the outer marginal end of an optic lens within a circumferential depression of an optic holder.
FIG. 6 is a sectional view of still another IOL assembly illustrating the construction or technique of adhesively securing the optic lens and optic holder together.
FIG. 7 is sectional view of still another IOL assembly depicting yet still another construction or technique for causing an optic lens to swellably engage within a corresponding complementary circumferential depression of an optic holder.

In FIG. 3 of the drawings, the optic lens 5a is shown as being complementary shaped relative to the interior configuration 13 of the optic holder 3a so as to provide mechanical engagement of the optic lens 5a within the optic holder 3a. As a result, there is a complementary interfitting fastening engagement between the optic lens 5a and the optic holder 3a, while also permitting disengagement therefrom when desired. Dimensional tolerances are important in this particular construction in order to achieve the desired complementary circumferential engagement, while permitting ready separation of the parts.

In the mechanical construction and technique shown in FIG. 4 of the drawings, the optic holder 3b and the optic lens 5b are shown as including complementary interfitting fastener parts is such as complementary fastener prongs and receptacles interconnecting the optic holder 3b and optic lens 5b together, while permitting ready separation therefrom. FIG. 4 thus represents the use of complementary interfitting male and female fastener elements which are configured, arranged and dimensioned to provide interfitting engagement with one another so as to readily retain the parts together, while permitting easy separation therefrom, when manually separated from one another. Threaded fastening elements also fall in this category.

The mechanical construction and technique illustrated in FIG. 5 of the drawings shows the optic lens 5c as being mounted within an inner circumferential depression or groove 17 of the optic holder 3c, thereby to provide the complementary interfitting fastening arrangement between the optic holder 3c and the optic lens 5c, while also permitting the parts to be readily separated from one another.

In FIG. 6 of the drawings, the optic holder 3d and optic lens 5d are shown as being secured together by an adhesive 19, either biologic or nonbiologic, as may be desired. It is important; however, that the adhesive 19 permit the optic holder and optic lens 3d, respectively, to be secured together during normal use, but readily permit the change of a new optic lens 5d, as may be desired, due to changing eye conditions. A variety of different types of adhesive, both biologic or nonbiologic type are disclosed in my copending patent application Ser. No. 07/306,691 filed Feb. 6, 1989 and entitled "IN- TRAOCULAR LENS IMPLANT AND METHOD OF LOCATING AND INHERING WITHIN THE POSTERIOR CHAMBER".

Still another construction or fastening technique is shown in FIG. 7 of the drawings where the optic holder 3e and optic lens 5e are secured together such as by swelling the parts into fixation with one another. In this regard, either the optic holder 3e or the optic lens 5e, or both may be constructed at 21 to allow change in the shape thereof during predetermined temperature changes, thereby allowing the parts to be swelled into releasable attachment to one another. This procedure is reversed for removing the optic lens 5 from the optic holder 3.

As previously indicated, the IOL assembly may include an optic lens releasably secured to the optic holder through a variety of mechanical and/or adhesive techniques or constructions. Thus, a holder having the releasable mechanical fastening means as shown in FIGS. 3-5 and 7 can also include a releasable adhesive 19 such as disclosed in the FIG. 6 releasable adhesive technique or construction.

Numerous other constructions and fastening techniques, such as through threading connection, adhesive, as a biological or nonbiological glue, as aforesaid, including fibrin, which will permit releasable fastening for securing the optic lens 5 to the optic holder 3 will be understood as also coming within the scope of the present invention, with the above examples of FIGS. 3-7 serving as various representative constructions or techniques which have been found useful in various circumstances.

It will now be appreciated that the IOL assembly of the present invention enables the optic holder 3 to be readily mounted within the posterior chamber 7 of an eye, while enabling the optic lens 5 to be removed and replaced with a suitable intraocular lens power in a new optic lens 5, without removing the optic holder from the posterior chamber 7 of the eye. The economies and efficiencies of the IOL assembly, together with the minimizing of surgical procedures and associated trauma provides a new and improved product that can be used whenever IOL implantation is desired.

In view of the above, it will be seen that the several objects and features of this invention are achieved and other advantageous results obtained.

As various changes could be made in the above constructions without departing from the scope of the invention, it is intended that all matter contained in the above description or shown in the accompanying drawings shall be interpreted as illustrative and not in a limiting sense.

I claim:

1. In an intraocular lens (IOL) assembly for implanting in the posterior chamber of a human eye after an extracapsular extraction, said IOL assembly including:
    an optic holder including haptic means for locating and positioning said optic holder in fixed position within said posterior chamber, and said haptic means includes flexible and resilient haptic elements integrally attached to the optic holder for implanting said optic holder within said posterior chamber, said haptic means comprising two generally opposed flexible and resilient haptic elements having reversely curving free ends associated therewith, said optic holder including said haptic means being formed as a one-piece unit, said optic holder including said intergral haptic means being formed from one of polymethylmethacrylate, polypropylene, hydrogel, or silicone material, an optic lens releasable secured to said optic holder for interchange of different optic lens without removing the entire optic holder, said optic lens and optic holder including complementary interfitting fastener means for securing said optic lens and optic holder together, said complementary interfitting fastener means including complementary interfitting male and female elements, said interfitting means including a circumferential depression formed in said optic holder, for receipt of an outer free end of said optic lens, said optic lens and optic holder being constructed from a material which will cause the optic lens to swell into engagement with the optic holder when brought into engagement therewith, said optic lens being releasably adhesively secured to said optic holder, and wherein said optic lens being made from polymethylmethacrylate, polycarbonate, hydrogel, or silicone material.

* * * * *